United States Patent [19]

Lanier

[11] Patent Number: 5,026,541
[45] Date of Patent: Jun. 25, 1991

[54] DISPOSABLE FINGERNAIL POLISH REMOVING DEVICE

[76] Inventor: Ann M. Lanier, 1523 Field Rd., Sarasota, Fla. 34231

[21] Appl. No.: 363,970

[22] Filed: Jun. 7, 1989

[51] Int. Cl.$^5$ ................................................. A61K 7/04
[52] U.S. Cl. ........................................ 424/61; 132/73; 132/73.5; 132/73.6
[58] Field of Search ................... 424/61; 132/73, 73.5, 132/73.6; 15/244.1

[56] References Cited

U.S. PATENT DOCUMENTS

| | | | |
|---|---|---|---|
| 3,124,825 | 3/1964 | Iovenko | 424/61 |
| 3,369,553 | 2/1968 | Keesee | 132/73.5 |
| 4,530,726 | 7/1985 | Montiel | 134/6 |
| 4,938,347 | 7/1990 | Tillman | 132/73 |

Primary Examiner—Merrell C. Cashion, Jr.
Assistant Examiner—D. Gabrielle Phelan
Attorney, Agent, or Firm—Charles J. Prescott

[57] ABSTRACT

A disposable fingernail polish removing device structured to be worn on the end of one finger while removing old fingernail polish from another fingernail. The device includes an inner cover of very thin, non-porous material and an outer layer connected over the inner cover and formed of somewhat compressible, absorbant material such as felt, compressed cotton, sponge material, or the like. When the device is placed over the end of one finger and liquid nail polish remover is disbursed into the outer layer, another fingernail may be rubbed with the outer surface of the device to remove its old fingernail polish. Because the inner cover is non-porous, the nail polish on the fingernail over which the device is placed is protected. Additional structure is provided for enhanced nail polish removal along the base and side margins of fingernails.

8 Claims, 1 Drawing Sheet

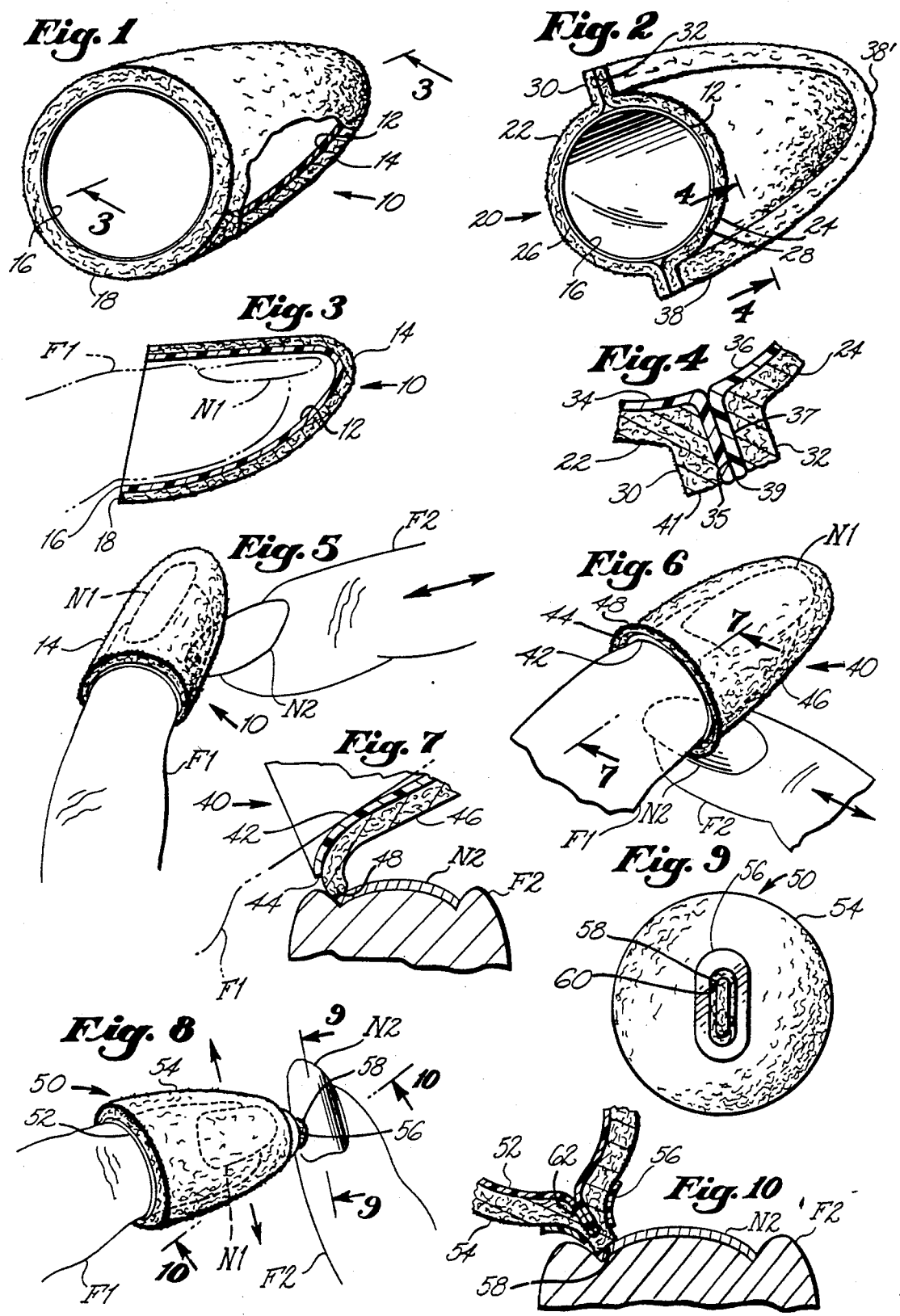

DISPOSABLE FINGERNAIL POLISH REMOVING DEVICE

BACKGROUND OF THE INVENTION

The present invention relates generally to devices for removing fingernail polish from the fingernails or toenails, and more particularly to a disposable device for removing fingernail polish from selected fingernails while protecting the polish on the fingernail over which the device is placed for use.

In many instances, the user of fingernail polish encounters objects which will chip or scratch the fingernail polish on one or more fingers. In such instances, particularly according to Murphy's Law, this occurs very shortly after polish has been applied. The appropriate mode of repair would be to remove the polish from only the damaged nail(s), while leaving the remaining nails intact until the normal life span of a fresh coat of fingernail polish is utilized.

However, in effecting repair of only one or a few damaged nails, typically fingernail polish remover, a strong solvent, will come in contact with undamaged fingernails and result in the removal of nail polish from substantially all of the fingernails instead of just the ones desired to be repaired.

In addition to conventional tissue and cotton balls for this purpose, applicant is aware of several devices which are utilized in conjunction with liquid fingernail polish remover to remove fingernail polish from fingernails. One such device is disclosed in Keesee U.S. Pat. No. 3,369,553 which includes an inner layer of compressible foam material, an outer cup-shaped rigid thin-wall support for the foam and a peg and apertured disc for supporting the entire arrangement in upright fashion. The mode of use is to insert the entire finger into the arrangement which has been saturated with fingernail polish remover.

Another similar device is disclosed in Spector U.S. Pat. No. 4,671,306 which discloses a thimble-shaped arrangement having a compressible foam insert which includes a slit centrally located for receiving the end of a finger. Again, the foam material is saturated with fingernail polish remover to effect cleaning.

One non-related invention known to applicant is disclosed in Tundermann U.S. Pat. No. 3902,509 which is directed to a disposable device for cleaning teeth wherein the device is placed over the end of the finger for rubbing abrasion against the surfaces of teeth to effect minor cleaning thereof.

The present invention discloses a device for removing fingernail polish from one finger while completely protecting the polish on the finger over which the device is placed. Several embodiments are provided, including additional structure to enhance the removal of fingernail polish from around the margins, i.e. the base and sides, of the fingernail against the raised tissue area of the end of the finger from which polish is somewhat more difficult to remove.

BRIEF SUMMARY OF THE INVENTION

This invention is directed to a disposable fingernail polish removing device structured to be worn on the end of one finger while removing old fingernail polish from another fingernail. The device includes an inner cover of very thin, non-porous material and an outer layer connected over the inner cover and formed of somewhat compressible, absorbant material such as felt, compressed cotton, sponge material, or the like. When the device is placed over the end of one finger and liquid nail polish remover is disbursed into the outer layer, another fingernail may be rubbed with the outer surface of the device to remove its old fingernail polish. Because the inner cover is non-porous, the nail polish on the fingernail over which the device is placed is protected. Additional structure is provided for enhanced nail polish removal along the base and side margins of fingernails.

It is therefore an object of this invention to provide a disposable device for the removal of fingernail polish from one finger while protecting the fingernail polish of the finger over which the device is used.

It is another object of this invention to provide additional improved structure to facilitate removal of fingernail polish around the base and side margins of a fingernail.

In accordance with these and other objects which will become apparent hereinafter, the instant invention will now be described with reference to the accompanying drawings in which:

BRIEF DESCRIPTION OF THE DRAWINGS

FIG. 1 is a perspective view of the preferred embodiment of the invention.

FIG. 2 is a perspective view of an alternate embodiment of the invention.

FIG. 3 is a section view in the direction of arrows 3—3 in FIG. 1 showing its positioning over the end of a finger in phantom.

FIG. 4 is an enlarged section view in the direction of arrows 4—4 in FIG. 2, except showing an alternate structure of the inner cover to that shown in FIG. 2.

FIG. 5 is a pictorial view of the invention as shown in FIG. 1 in use.

FIG. 6 is a pictorial view of yet another embodiment of the invention shown in use.

FIG. 7 is an enlarged section view in the direction of arrows 7—7 in FIG. 6.

FIG. 8 is a pictorial view of yet another embodiment of the invention in use.

FIG. 9 is an end view in the direction of arrows 9—9 in FIG. 8.

FIG. 10 is a section view in the direction of arrows 10—10 in FIG. 8.

DETAILED DESCRIPTION OF THE INVENTION

Referring now to the drawings, and more particularly to FIGS. 1, 3 and 5, the preferred embodiment of the invention is shown generally at 10 and includes an inner, very thin-walled molded cover 12 fabricated of plastic and structured to snuggly but comfortably fit over the end of a finger F1 by insertion into the opening 16 of inner cover 12. Disposed over the outer surface of the cover 12 is a layer of felt material 14 which is somewhat thicker and more compliant in nature and capable of absorbing both a quantity of liquid fingernail polish remover and collecting dissolved old fingernail polish which is to be removed by the device 10. As best seen in FIG. 5, the device 10 is placed over the end of one finger F1 while a fingernail N2 finger F2 is rubbed transversely against the outer cover 14 which has been saturated with fingernail polish remover. By this means, all fingernail polish is removed from fingernail N2.

A unique feature of this invention is that, because of the non-porous nature of the inner cover 12, the liquid fingernail polish remover is not able to come in contact with fingernail N1 of the finger F1 over which the device 10 is placed. This feature, when desired, allows the user to selectively remove damaged fingernail polish from one or more selected fingernails N2 while protecting the fingernail polish disposed on the fingernail N1 over which this device is placed.

Referring now to FIG. 2, an alternate embodiment of the invention is shown generally at 20 and includes the same very thin, non-porous molded plastic inner cover 12. However, this embodiment includes an outer cover which is fabricated of mating outer cover portions 22 and 24 which are fabricated of a sponge-like material which is also somewhat compressible and able to absorb and retain a quantity of fingernail polish for use in rubbing against a fingernail as previously described.

The mating outer layer halves 22 and 24 are seamed or heat-sealed together to form a flange-like structure 30/32. This flange 30/32 provides an outwardly extending edge margin 38 which is particularly useful in removing fingernail polish around the side and base margins of the fingernail adjacent the skin of the fingertip as will be herebelow described with respect to other embodiments of the invention. Thus, the tip 38' of peripheral edge 38 is particularly useful for this purpose.

Referring additionally to FIG. 4 in conjunction with FIG. 2, an alternate structure for the inner cover formed of mating inner cover halves 34 and 36 is there shown. These inner cover halves 34 and 36 are also fabricated of very thin, non-porous plastic material, but include flanges 35 and 37 which mateably engage and are heat sealed together so as to form outer peripheral edge 39. The mating outer layer halves 22 and 24 are matingly connected against the outer surfaces of the flanges 35 and 37 instead of onto themselves to form peripheral margin 41 for use in a fashion similar to that with respect to FIG. 2.

Referring now to FIGS. 6 and 7, another embodiment of the invention is shown generally at 40 including a very thin-wall molded, non-porous plastic inner cover 42 having a somewhat more compressible and absorbent outer cover 46 disposed thereover. In this embodiment 40, the inner cover 42 includes an outwardly extending radial flange 44 which redirects the absorbent outer cover 46 radially outwardly thereagainst to form edge 48. This edge 48 is useful in removing fingernail polish from immediately adjacent the side margins of the fingernail N2 of FIG. F2 while rubbing the device in place over finger F1 as shown. This edge 48, being redirected outwardly and stiffened and supported by flange 44 is effective for this purpose.

Referring now to FIGS. 8, 9 and 10, another alternate embodiment of the invention is shown generally at numeral 50 and is structured to more specifically facilitate removal of old fingernail polish from adjacent the side and base margins of the fingernail N2. In this embodiment 50, the inner cover 52, formed of very thin, non-porous plastic molded material, includes an inner tip 62 as best seen in FIG. 10. The outer cover 54 is formed over the entire inner cover 52 and the inner tip 62, which is held in the configuration best seen in FIG. 10 by a molded, very thin plastic collar 56 having aperture 60 disposed therethrough. Collar 56 is adhered or heat sealed onto the end of outer cover 54 so that inner tip 52 forces the surrounding outer cover material 54 through aperture 60 of collar 56 so as to form outer tip 58 of absorbent outer cover material. By this arrangement, as best seen in FIGS. 8 and 10, the outer tip 58 may be utilized to effectively remove old fingernail polish from adjacent the side and base margins of fingernail N2. Although not preferred because of lack of durability, the collar 56 may be eliminated and the outer layer 54 may be molded into the configuration of outer tip 58 over inner tip 62.

In all embodiments, the absorbent outer layer may also be a foam material. Additionally, by using self-skinning molding techniques, the outer layer may be so molded wherein the inner surface is self-skinning and having sufficient density so as to eliminate the need for a separate inner cover. In such case, the self-skinning inner surface of the molded outer layer becomes the nonporous inner cover.

While the instant invention has been shown and described herein in what is conceived to be the most practical and preferred embodiment, it is recognized that departures may be made therefrom within the scope of the invention, which is therefore not to be limited to the details disclosed herein, but is to be accorded the full scope of the claims so as to embrace any and all equivalent apparatus and articles.

What is claimed is:

1. A disposable fingernail polish removing device structured to be worn on a first finger end to remove old fingernail polish from a nail of a second finger comprising:
   an elongated inner finger end cover having an end opening and formed of generally non-porous material structured to allow insertion of a first finger end thereinto;
   a porous compressible outer layer connected over, and generally coextensively covering, said inner cover, said outer layer structured to absorbently receive a quantity of liquid fingernail polish remover and to absorb and collect old fingernail polish from the nail of a second finger as said outer layer is rubbed transversely against the second fingernail when said device is worn on the first finger end;
   said inner cover preventing liquid fingernail polish remover from coming into contact with fingernail polish on the fingernail of the first finger.

2. A disposable fingernail polish removing device as set forth in claim 1, wherein:
   said inner cover is molded plastic;
   said outer layer is felt material.

3. A disposable fingernail polish removing device as set forth in claim 1, wherein:
   said outer layer is flexible foam material.

4. A disposable fingernail polish removing device as set forth in claim 3, wherein:
   said outer layer is molded of self-skinning foam wherein said inner cover is integrally formed of said self-skinning foam material when said device is molded.

5. A disposable fingernail polish removing device as set forth in claim 1, wherein:
   said outer layer is formed of two longitudinal halves whose mating margins are connected together to form a seam line which outwardly extends from said outer layer along at least a portion of the length of said outer layer;
   said seam line structured for enhanced fingernail polish removal along the base and side margins of the second fingernail.

6. A disposable fingernail polish removing device as set forth in claim 5, wherein:
said inner cover is formed of two longitudinal halves whose mating margins are connected together to form a seam line which laterally extends outwardly from said inner cover and is disposed and connected within at least a portion of said outer layer seam line;
said inner cover seam line stiffening and supporting said outer layer seam line for further enhanced fingernail polish removal along the base and sides of the second fingernail.

7. A disposable fingernail polish removing device as set forth in claim 1, wherein:
said inner cover opening includes a laterally radially outwardly extending flange;
said outer layer also laterally radially outwardly extending somewhat beyond said flange, but is supported and stabilized by said flange whereby fingernail polish removal along the base and sides of the second fingernail is enhanced.

8. A disposable fingernail polish removing device as set for in claim 1, wherein:
a molded collar having a central hole and connected over the end of said outer layer;
the portion of the end of said outer layer compressed and formed through said hole to form a tip whereby fingernail polish removal along the base and sides of the second fingernail is enhanced.

* * * * *